United States Patent [19]

Bucknell et al.

[11] Patent Number: 6,111,653
[45] Date of Patent: Aug. 29, 2000

[54] TRANSLUCENCY MEASUREMENT

[75] Inventors: Stephen Paul Bucknell, Salisbury; Nigel John Peter Winsey, Sandhurst; Desmond Roy Gale, Andover, all of United Kingdom

[73] Assignee: Dia-Stron Limited, United Kingdom

[21] Appl. No.: 09/037,163

[22] Filed: Mar. 10, 1998

[51] Int. Cl.[7] .................................................. G01B 9/02
[52] U.S. Cl. .......................................... 356/446; 356/445
[58] Field of Search .............................. 356/73, 317, 318, 356/319, 326, 328, 371, 416, 417, 419, 445, 446

[56] References Cited

U.S. PATENT DOCUMENTS

| 4,397,554 | 8/1983 | Genco et al. ............................ 356/239 |
| 4,801,804 | 1/1989 | Rosenthal ................................ 250/341 |
| 4,884,891 | 12/1989 | Borsboom ............................... 356/446 |
| 5,926,262 | 7/1999 | Jung et al. ................................ 356/73 |

FOREIGN PATENT DOCUMENTS

| 0 032 774 A2 | 7/1981 | European Pat. Off. ....... G01N 21/55 |
| 0 074 428 A1 | 3/1983 | European Pat. Off. ....... G01N 21/47 |
| 0 099 023 A2 | 1/1984 | European Pat. Off. ....... G01N 21/47 |
| 0 211 465 A2 | 2/1987 | European Pat. Off. ....... G01N 21/47 |
| 0 360 738 A1 | 3/1990 | European Pat. Off. ........... G01J 3/46 |
| 0 580 414 A2 | 1/1994 | European Pat. Off. .......... A61B 5/00 |
| 0 627 619 A1 | 12/1994 | European Pat. Off. ....... G01N 21/47 |
| 0 627 620 A1 | 12/1994 | European Pat. Off. ....... G01N 21/47 |
| 0 656 536 A1 | 6/1995 | European Pat. Off. ....... G01N 21/47 |
| 0 703 445 A2 | 3/1996 | European Pat. Off. ....... G01N 21/47 |
| 295 12 741 U1 | 11/1995 | Germany ..................... G01B 11/14 |
| 2 269 012 | 1/1994 | United Kingdom .......... G01N 21/27 |
| 2 304 187 | 3/1997 | United Kingdom .......... G01N 21/49 |

*Primary Examiner*—Frank G. Font
*Assistant Examiner*—Michael P Stafira

[57] ABSTRACT

The translucency of a material is determined by illuminating the material and detecting the intensity of radiation leaving the material as a function of distance from the radiation source. The resulting measurements may be used to determine a "translucency gradient" for the material. In the case of materials in sheet form or having a defined thickness, the translucency can be measured in transmission mode or back scattering mode to measure "through translucency" or "surface translucency".

17 Claims, 3 Drawing Sheets

TRANSLUCENCY MEASUREMENT

The present invention relates to the measurement of the translucency of a material.

Translucent materials—that is materials which both diffuse and allow a significant amount of light to pass through them—have a variety of applications. One application is in the field of lighting. Translucent materials are used for light bulbs and fluorescent tubes rather than transparent materials, for example, because they diffuse the light and reduce glare which can irritate the eyes.

Other applications for translucent materials include paints and pigments, since translucent coatings may be more aesthetically pleasing than opaque coatings.

The measurement of translucency is useful in food science, since most foods, especially fluids, are translucent and this has a large effect upon their visual appearance to customers. Translucency measurement would also be useful in process control as, for example, the translucency of milk varies with fat content.

At the moment, there appears to be no universally accepted method for measuring the translucency of a material in order to assess its suitability for a particular application. In fact there appears to be no scientific definition of translucency. Frequently, measurement is subjective and materials are judged "by eye". It is routine to measure the total amount of light passing through a material, sometimes known as "diffuse transmission", to determine its translucency but this measurement gives limited information about the light diffusing properties of a material. In particular, the diffuse transmission of a material does not quantify its ability to laterally spread light.

As well as indicating the suitability of a material for a particular application, translucency measurement can also indicate the condition of materials likely to decay, such as foods, and the condition of living or regenerated materials, such as human skin. Measurements on human skin have other uses, such as determining the efficacy of creams and ointments for the treatment of skin conditions including ageing.

A method of measuring the "surface translucence" of human skin has been proposed by C. W. Hargens in Bioengineering Newsletters, 1979 Vol. 2, page 319 in an article entitled "The surface translucence meter: its use in studying human skin". By "surface translucence", Hargens means light entering and returning from the surface. The expression "surface translucency" will be used in the same context in the following description. This is distinguished from translucence from one side of a material to the other (hereinafter "through translucency") which might be of more interest in the lighting industry, for example. Hargens measures surface translucency by illuminating an area of the surface of a material, using a light barrier to shield reflected light, and measuring the total amount of light returning from the surface in an area adjacent to the illumination area. Whilst this produces useful information about the translucency of a material, the present invention is based on the discovery that more informative results can be achieved by measuring the amount of light returning from a material as a function of distance from the illumination source. As the following analysis will show, a material of apparently low translucence looks quite different when examined according to the method of the invention. The invention applies equally to surface translucence measurement and translucence from one side of a material to the other.

The present invention provides a method of determining the translucency of a material including illuminating the material with a radiation source, measuring the intensity of radiation leaving the material as a function of distance from the point or area of illumination, and determining the rate of change of the intensity as a function of said distance. The rate of change is hereinafter referred to as the "translucency gradient" of the material. The translucency gradient is determined by exponential curve fitting, Here the term "exponential" is used in its widest sense so that exponential curve fitting includes fitting experimental data to a formula in which intensity and distance are related by a power factor.

The preferred radiation is visible light. The material may be solid, liquid or gas.

Typically, a material sample is illuminated at a point or area on its surface and the intensity of light leaving the material is measured at other parts of the same surface of the material. The result is an indication of the surface translucency of the material.

When examining materials in the form of films or sheets, a point or area on one major surface of the material may be illuminated and the intensity of light leaving the opposite major surface of the material may be measured. The result is an indication of the "through translucency" of the material.

With fluids, it may be necessary to define a boundary of the material, for example by means of some sort of physical barrier. Thus, the term "surface" should be understood to include a boundary for liquids or gases.

For uniform materials it may be adequate to measure the intensity of returning light at various points or areas at different distances from the light source or illumination point. However, it is preferable to measure the total light emanating from the surface of a material at any particular distance from the source or illumination point. This may be approximated by measuring the total amount of light leaving defined areas of the material, the areas being in the form of concentric rings surrounding the light source or illumination point. Preferably the concentric rings are of equal width. Alternatively they may have equal areas so that the larger the ring, the smaller its width. Preferably there are no spaces between adjacent rings.

Preferably the method according to the invention includes the step of physically excluding from the measuring means (e.g. light detectors) any light which has been reflected directly from the surface of the material or, in the case of "through translucency" measurement excluding any light which has passed straight through the material without scattering.

The measurement of translucency of a living sample such as human skin could be combined with other measurements such as surface roughness and colour, and indexed with other factors such as age, sex, humidity and temperature, to devise a "skin index" for the sample in the form of a single numerical value. The determination of a skin index for different samples would enable them to be compared more readily. The "skin index" could be determined by a neural network which compares the test results with stored data.

The invention also provides apparatus for measuring the translucency of a material comprising a radiation source and means for measuring the intensity of radiation leaving the material at several different distances from the illumination point or area of the material.

Preferably, the source is a source of visible light. However, any electromagnetic radiation may be used and wavelengths in the ultra violet or infra red regions may be useful.

Preferably the apparatus includes a plurality of detectors positioned at different distances from the source or where the radiation is guided from the source to the material. The detectors may be at different distances from the exit point of the radiation from the apparatus, possibly in a linear array. Alternatively, an array of individual detectors, usually light detectors, may be provided, arranged in groups with each group forming a ring about the source or exit. Alternatively each detector may be in the form of a ring arranged about the source. Either way concentric rings of increasing diameter may be provided about the source or exit. Means may be provided for preventing radiation travelling directly from the source or reflected directly from the source from reaching the light detectors.

Apparatus according to the invention may be provided for measuring the through translucency of a material, in which case the detectors are positioned on the opposite side of the material to the source. Alternatively, in order to measure surface translucency the detectors are arranged to detect radiation which is scattered back from the surface of the material which has been illuminated. Then, the detectors may be in the same plane as the source or radiation exit.

To enable the apparatus to be placed in contact with the material and to isolate electrical parts of the apparatus from the material, means may be provided for guiding the radiation from the source to the material, such as a fibre optic bundle, and means may be provided for guiding radiation back to the detectors. The latter means may comprise further fibre optic bundles but rod lenses of low numerical aperture may be used to avoid "cross talk", e.g. to avoid light from one area being detected by a detector for another area. The individual optical fibres may be replaced by a single fibre optic "faceplate" to be described below. The source, detectors, guide means, associated electronics and signal processing may be provided in a single assembly.

Apparatus according to the invention may include means for measuring other parameters of the material.

It will be appreciated that the method of the invention can be performed without the apparatus described above. Instead it would be possible to use a single detector in conjunction with a movable light source which is swept across the surface of the material being examined.

An embodiment of the invention will now be described by way of example only and with reference to the accompanying drawings in which.

Figure 1:
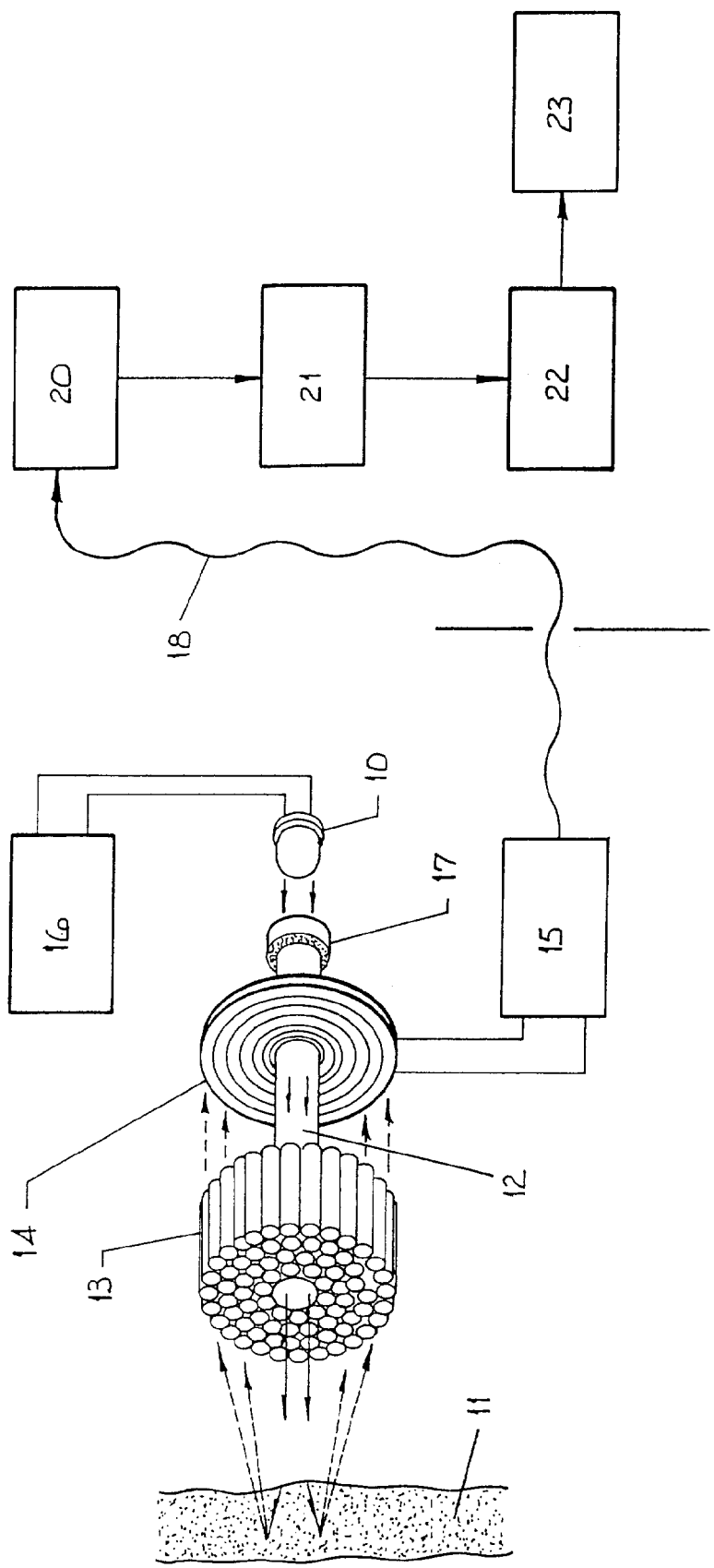
FIG. 1 is a schematic diagram of apparatus for measuring translucency according to the present invention.

The apparatus of FIG. 1 includes a high intensity LED 10 for illuminating a test material 11. Light from the LED is focused by a miniature lens, not shown, and conducted along a fibre optic bundle 12 to the material 11. The end of the fibre optic bundle 12 is surrounded by an array of miniature rod lenses 13 which are arranged in concentric rings. Light collected by the lenses 13 travelling away from the sample is focused on a specially constructed silicon photodetector 14. The fibre optic bundle 12 may be replaced by a single fused fibre optic block which avoids the need for several discrete cables.

The photodetector 14 consists of concentric annular rings about the fibre optic bundle 12.Thus, each ring of rod lenses 13 corresponds to a ring of photodetector 14, and each ring of photodetector 14 receives light leaving the sample 11 at a particular radial distance from the illumination point, whereby each ring of the photodetector produces a signal representing the light intensity at a particular radial distance, integrated over 360 degrees.

In the presently preferred embodiment of the invention, the bundle 12, and rod lenses 13 are replaced by a "faceplate" material supplied by Schoff Glass which enables the measurement surface to be mapped onto the detector array. This "faceplate" consists of miniature glass rods fused into a solid material.

Signals from the photodetector rings are recorded by suitable LSl analogue electronics generally indicated at 15. The electronics and the light source 10 are powered by a battery 16. It will be appreciated that other power sources could alternatively be used. An interference filter 17 is provided for use in selecting the appropriate wavelength light from the LED 10.

The components of the apparatus described above constitute a probe assembly which is applied to the sample under test. The assembly is connected via flexible cable 18 to a notebook PC which includes analogue to digital converter 20 and software generally indicated at 21. The PC includes a neural network 22 which is used to derive a skin index indicated at 23, to be described in more detail below. An alternative embodiment of apparatus according to the invention is a complete hand held system employing a suitable microcontroller for signal processing means.

Figure 2:
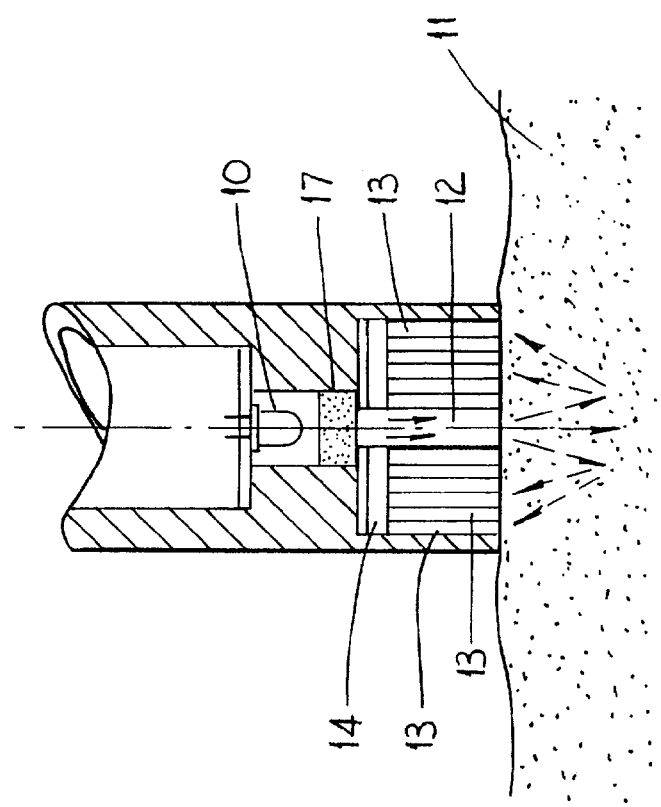

FIG. 2 shows the probe assembly of FIG. 1 in position for determining the translucency gradient according to this invention. The probe assembly is positioned in contact with the test material 11. Thus almost all light which is reflected from the surface of the material will be passed back along the fibre optic bundle 12 and will not reach the lenses 13. The lenses 13 only receive light which has entered the sample and been laterally scattered, as indicated. This is the process of light diffusion. The degree of spread depends principally on the size, distribution and absorption coefficient of the scattering centres in the material.

The probe assembly has a number of significant features as follows: High intensity LEDs are used rather than a halogen light source, for example, because they are more efficient and generate less heat and therefore enable the probe assembly to be battery powered. The miniature rod lenses have low numerical apertures and map the emergent light onto specific rings of the detector 14. By using such lenses, cross talk between adjacent lenses is minimised. The lenses enable the sample 11 to be spaced from the photodetector 14 to minimise any capacitive coupling between sample and detector.

In fact, the sample does not come into contact with any electric circuit.

Figure 4:
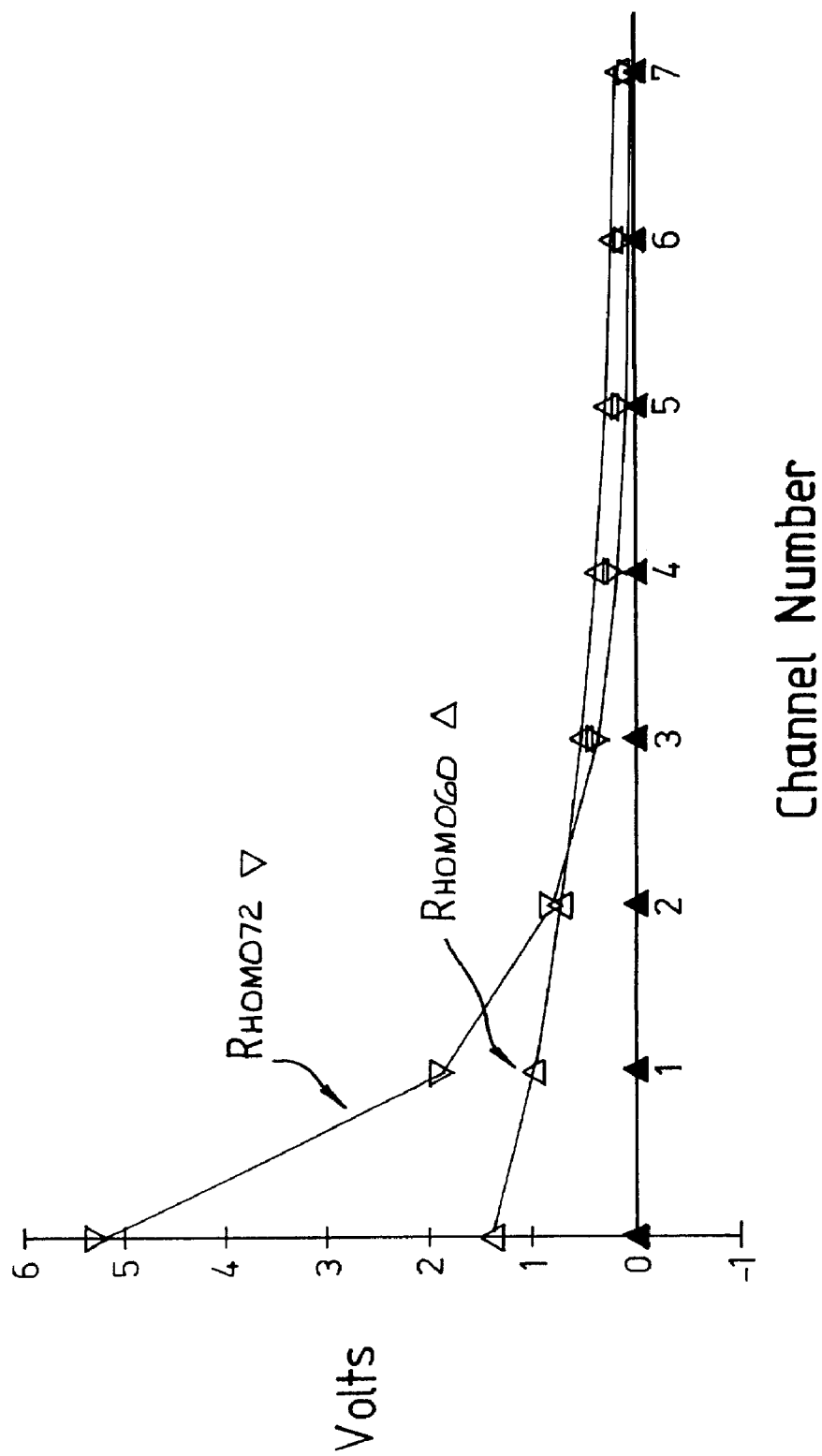
FIG. 4 is graph of light intensity versus distance from point source for two different test materials.

The following table shows the results of measurements made on two samples of materials using an experimental rig consisting of a multi-layer fibre optical probe arranged such that the central bundle acts as light source, and concentric rings of fibre optic wrapped around the source in "onion skin" fashion convey back scattered light to detectors. Each complete ring feeds a single channel in the data acquisition system, channel 1 being adjacent the light source. Each channel is separated from the next by a baffle so that light incident on each fibre optic can only come from within the sample. The test results are shown graphically in FIG. 4.

|  | Sample 1 RHOM 072 | Sample 2 RHOM 060 |
| --- | --- | --- |
| Channel 1 | 5.255 | 2.478 |
| Channel 2 | 1.859 | 1.468 |
| Channel 3 | 0.792 | 0.949 |

-continued

|  | Sample 1<br>RHOM 072 | Sample 2<br>RHOM 060 |
|---|---|---|
| Channel 4 | 0.362 | 0.621 |
| Channel 5 | 0.176 | 0.421 |
| Channel 6 | 0.079 | 0.282 |
| Channel 7 | 0.038 | 0.191 |
| Channel 8 | 0.027 | 0.137 |
| Ratio 1:8 | 194.63 | 18.08 |
| Integral | 8.588 | 6.547 |
| % Transmission | 19% | 44% |
| $\mu_L$ (see below) | −0.762 | −0.410 |

Two test samples were used, both plastic tiles (PMMA) supplied by RHOM Ltd. They are sold under the trade name PLEXIGLAS and have a white cloudy appearance.

Sample 1 was RHOMO72 which has an optical transmission half that of sample 2, RHOMO60. Subjectively, sample 1 is much more opaque than sample 2 and would appear to have less diffuse glow.

Sample 1 shows high light intensity close to the source indicating that light is being scattered out of the material very rapidly. The curve then quickly declines approaching zero signal for channels 6 and 7. The high concentration of scattering centres (low transmission) results in very little light scattering laterally away from the source.

Sample 2 shows a marked difference. The intensity VS distance curve is much flatter, appreciable amounts of light being collected in channels 6 and 7. The lower light intensity in channel 1 arises because a) more light passes straight through the sample (higher transmission figure) and b) that light which is scattered travels further between scattering events and so is not localised around the source.

The total diffuse glow (as calculated by integrating the area under the curve) for sample 1 is greater than that for sample 2 thus ranking it as having a higher surface translucency by Hargens' method.

Measuring the gradient of the curves by exponential curve fitting, shows that sample 2 has a lower surface translucency gradient and according to the above explanation, has superior surface translucency properties. This is contrary to the result from tiargens' method and agrees with visual assessment.

The measurement of translucency gradient, may be stored with other parameters to provide an index for translucent materials with which new materials may be compared Experimental data obtained to date indicates that exponential curve fitting, ie fitting the data to a power relationship is the preferred method for obtaining a figure denoting translucency gradient. Provided diffraction is negligible, the transmission of light can be considered similar to the diffusion of particles through a scattering matrix in which case:

$$\text{Intensity} = I_o \exp(-\mu x) \quad (1)$$

where:
 $I_o$=Intensity of illumination
 x=Distance into material
 $\mu$=photon mean free path.

The photon mean free path characterises the material and is dependant upon scattering centre concentration, size and wavelength of illuminating light.

The lateral spread of light in a material is governed by a function of similar form, modified by the angular distribution of the scattering, thickness of the material in relation to the photon mean free path and absorption coefficients. The curves shown in FIG. 4 can be fitted to equation of the general form Lateral Intensity $A^{by}$ where A is a constant, y is the lateral distance across the material and b is another constant indicative of the translucency of the material. Thus, solving for b gives a measure of the translucency. The data given above has been fitted to the equation $$\text{Lateral Intensity} = I_o \exp(\mu_L y) \quad (2)$$

where: $\mu_L$ is termed the effective translucent photon mean free path.

In the preferred embodiment of the invention, $\mu_L$ is used as an indication of the translucency gradient. Values of $\mu_L$ for the samples are given in the tables above.

Equation (2) is an empirical function which has been found to fit the data well $\mu_L$ is not the same as $\mu$ although our experimental results show a clear dependancy between $\mu_L$ and photon mean free path. We anticipate that changes in $\mu_L$ can be correlated with physical changes in the sample under test by the use of predetermined calibration samples. The choice of calibration samples will be unique for each specific application of the invention, depending on which properties of the material affecting its translucency are of interest.

$\mu_L$ is the preferred way of characterising the translucency of a material for many reasons. One reason is that a two point measurement (linear gradient) cannot be used to accurately predict the light intensity at any given distance from the source as the light distribution is clearly non-linear. Also, the determination of $\mu_L$ is independent of the intensity of the light source and thus it is preferable to the Hargens method described above.

Measurement of surface or through translucency is affected by reflections from boundary interfaces in this film samples. This is especially the case where the sample thickness is less than twice the photon mean free path $\mu$.

The present invention is particularly useful in the examination of human skin. Parameters such as translucency gradient, total diffuse glow (the integration measurement discussed above) colour balance, surface roughness, age, sex, humidity, temperature and so on may be taken into account when determining a "skin index". Referring back to FIG. 1, a neural network could be used to examine the condition of new skin samples based on stored knowledge and "taught" information provided by showing the network examples of good and bad skin. Thus, as indicated in FIG. 1 the network 22 would derive the skin index 23. The use of a neural network is particularly desirable because the network itself will decide how much "weight" to give the parameters according to its own rules based on its teaching.

In fact, the probe assembly of FIG. 1 can also be used to determine colour balance and surface roughness as explained below.

The ability to select the light wavelength using filter 17 enables the apparatus to be used for measuring the colour of a sample as well as its translucency. Choice of wavelength depends on the particular material being examined. For human skin, light tuned to the absorption bands of skin chromophores is most appropriate. As the collected light has passed through the sample, it carries information relating to absorption of the selected wavelength, so that the detected intensities of light can be used to determine a colour balance of the sample. Colour balance would be measured in the mode shown in FIG. 2.

Figure 3:
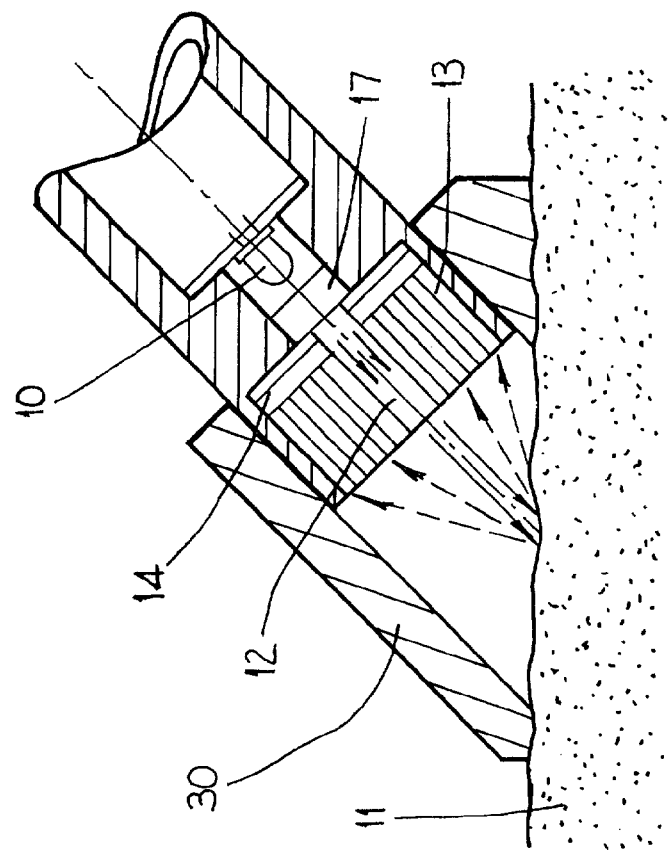
FIGS. 2 and 3 illustrate two possible modes of operation of the apparatus of FIG. 1.

FIG. 3, shows how the assembly can also be used in a "non-contact" mode to determine surface roughness. The probe assembly is positioned spaced from the sample, preferably with the fibre optic bundles 12 inclined to the sample surface. A shield 30 may be provided for positioning the probe assembly and excluding ambient light. In the mode shown in FIG. 3, the probe receives mainly light reflected from the surface of the sample although some diffused light will also reach the lenses. The angle of reflection of the light will depend on any irregularities in the surface of the material and the distribution of light received at the photodetector 14 will therefore be indicative of surface roughness. A surface roughness index can be determined by taking the ratio of backscatter normal to and at 45 degrees to the sample surface. The ratio measurement reduces any anomalies due to surface absorption.

It may be possible to modify the illustrated probe assembly to include means for measuring other parameters such as ambient temperature, ambient humidity and moisture content of the sample.

What is claimed is:

1. A method of determining the translucency of a material including illuminating the material at a point or area on its surface with a radiation source, measuring the intensity of radiation leaving the same surface of the material at several different lateral distances from the point or area of illumination using apparatus in contact with the surface and using exponential curve fitting to determine the rate of change of the intensity as a function of lateral distance from the point or area of illumination.

2. A method as claimed in claim 1 in which the measured intensity values are fitted to a formula of general form Intensity $A^{by}$ where A is a constant and y=Lateral distance from point of illumination to determine the value of b as an indication of said rate of change of intensity.

3. A method as claimed in claim 2 in which the measured intensity values are fitted to the formula Intensity=Io exp $(\mu_L\ y)$ where Io=Intensity of illumination.

4. A method as claimed in claim 1 in which the intensity of radiation travelling in the opposite direction to said radiation source is measured as a function of distance from the point of area of illumination.

5. A method as claimed in claim 1 in which the intensity of radiation travelling in the same direction as said radiation source is measured as a function of distance from the point or area of illumination.

6. A method as claimed in claim 1 including making a spectral analysis of the detected radiation in order to obtain additional information about the material.

7. Apparatus for measuring the translucency of a material comprising a radiation source, means for simultaneously measuring the intensity of radiation leaving the material at several different lateral distances from the point or area of illumination of the material and means for fitting intensity and distance measurements to an exponential curve to determine the rate of change of the intensity as a function of distance.

8. Apparatus as claimed in claim 7 including means for preventing radiation travelling directly from the source from reaching the detectors.

9. Apparatus as claimed in claim 7, arranged such that the material may be positioned between the source and the intensity measuring means.

10. Apparatus as claimed in claim 7 in which the intensity measuring means are arranged to detect radiation scattered back from the surface of the material.

11. Apparatus as claimed in claim 7 including means for analysing the spectrum of radiation scattered from the material.

12. Apparatus as claimed in claim 7 further comprising means for determining the surface roughness of the material from radiation reflected from the surface of the material.

13. Apparatus as claimed in claim 7 including means for selecting a particular wavelength or wavelength range from the source.

14. A method of determining the translucency of a material including illuminating the material at a point or area on its surface with a radiation source, measuring the intensity of radiation leaving an opposite surface of the material at several lateral distances from the point or area of illumination and using exponential curve fitting to determine the rate of change of the intensity as a function of lateral distance from the point or area of illumination.

15. A method as claimed in claim 14 in which the measured intensity values are fitted to a formula of general form:

Intensity $A^{by}$ where

A is a constant and y=Lateral distance from point of illumination to determine the value of b as an indication of said rate of change of intensity.

16. A method as claimed in claim 15 in which the measured intensity values are fitted to the formula:

Intensity=Io exp $(\mu_L\ y)$ where

Io=Intensity of illumination.

17. A method as claimed in claim 14 including making a spectral analysis of the detected radiation in order to obtain additional information about the material.

* * * * *